United States Patent
Hall et al.

(10) Patent No.: US 11,419,972 B2
(45) Date of Patent: Aug. 23, 2022

(54) WOUND THERAPY DEVICE, KIT, AND METHOD FOR IMPROVED APPLICATION TO WOUNDS ON COMPLEX GEOMETRIES

(71) Applicant: KCI LICENSING, INC., San Antonio, TX (US)

(72) Inventors: Colin J. Hall, Poole (GB); Benjamin A. Pratt, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 468 days.

(21) Appl. No.: 16/557,280

(22) Filed: Aug. 30, 2019

(65) Prior Publication Data
US 2020/0069853 A1 Mar. 5, 2020

Related U.S. Application Data

(60) Provisional application No. 62/726,567, filed on Sep. 4, 2018.

(51) Int. Cl.
*A61M 1/00* (2006.01)
*A61F 13/02* (2006.01)
(Continued)

(52) U.S. Cl.
CPC ........... *A61M 1/90* (2021.05); *A61F 13/0216* (2013.01); *A61F 13/0253* (2013.01);
(Continued)

(58) Field of Classification Search
CPC ....... A61M 1/90; A61M 1/86; A61F 13/0216; A61F 13/0253; A61F 13/061;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion in International Application No. PCT/US2019/049100, dated Nov. 22, 2019 (14 pages).

(Continued)

*Primary Examiner* — Susan S Su
*Assistant Examiner* — Eric Rassavong

(57) ABSTRACT

A negative pressure wound therapy device, kit, and method are provided for improved treatment of wounds on complex three-dimensional anatomies. The device includes a conformable manifold made of a porous and permeable material with a pattern of cuts designed to transform the manifold from a relaxed, planar state to a pliable three-dimensional state when extended along the lateral axis. The kit further may include a wound interface layer, an adhesive, breathable drape, and a pneumatic connection to a negative pressure wound therapy device. Finally, a method for treating wounds using reduced pressure and the presently disclosed kit is provided.

21 Claims, 12 Drawing Sheets

(51) Int. Cl.
*A61F 13/14* (2006.01)
*A61F 13/06* (2006.01)
*A61F 13/10* (2006.01)

(52) U.S. Cl.
CPC .......... *A61F 13/061* (2013.01); *A61F 13/066* (2013.01); *A61F 13/101* (2013.01); *A61F 13/145* (2013.01); *A61F 13/146* (2013.01); *A61M 1/86* (2021.05)

(58) Field of Classification Search
CPC .... A61F 13/066; A61F 13/101; A61F 13/145; A61F 13/146; A61F 13/00072; A61F 13/00068
See application file for complete search history.

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 10,046,095 | B1* | 8/2018 | Middaugh ............... A61M 1/80 |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2014/0094730 | A1* | 4/2014 | Greener ............ A61F 13/00038 602/46 |
| 2016/0287765 | A1* | 10/2016 | Canner ............ A61F 13/00995 |
| 2018/0228653 | A1* | 8/2018 | Kilpadi ................. A61F 13/512 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |

(56) References Cited

FOREIGN PATENT DOCUMENTS

| WO | 99/13793 A1 | 3/1999 | | |
|---|---|---|---|---|
| WO | WO-2015058114 A1 | * | 4/2015 | ............ A61B 5/6833 |
| WO | WO-2018134162 A1 | * | 7/2018 | ........ A61F 13/00068 |

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 pages English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

WOUND THERAPY DEVICE, KIT, AND METHOD FOR IMPROVED APPLICATION TO WOUNDS ON COMPLEX GEOMETRIES

CROSS-REFERENCE TO RELATED APPLICATIONS

This application claims the benefit of priority to U.S. Provisional Application No. 62/726,567, filed on Sep. 4, 2018, which is incorporated herein by reference in its entirety.

BACKGROUND

The present disclosure relates generally to medical treatment, and more particularly to reduced pressure wound treatment devices, kits, and methods.

Negative pressure wound therapy (NPWT) is a type of wound therapy that involves applying a negative pressure to a wound site to promote wound healing. Some wound treatment systems apply negative pressure to a wound using a pneumatic pump attached to a dressing covering the wound to generate the negative pressure and flow required. However, with NPWT, it is essential that a dressing, bandage or manifold accurately conform to a three-dimensional wound site, since the negative pressure applied to the dressing or bandage compresses the dressing to the wound surface. Thus, sizing and fit are integral elements in the efficacy of a NPWT device, in many instances more so than in standard wound treatments. Many NPWT dressings are improperly sized, ill-fitting, contain imperfections, do not conform to the contours of the anatomy of a three-dimensional wound site, or some combination of all these drawbacks. For example, many NPWT manifolds and dressings are not sized to fit rounded, asymmetric, or non-planar body parts, such as a knee, elbow, foot, shoulder, or breast. Specifically shaped dressings for such geometries, especially when considering variable body-sizes, require a multitude of dressing variants, often leading to an unmanageable number of individual stock-keeping units. Additionally, preformed three-dimensional dressings require larger packaging with increased space for storage and transportation. Accordingly, there is a need for an improved device, kit, and method that more accurately conform NPWT to a wide variety of three-dimensional wound sites and maximize shipping and storage space.

SUMMARY

The present technology overcomes the drawbacks of previous systems by providing a device, kit, and method for improved negative pressure wound therapy to wounds on complex geometries. One implementation of the disclosure is a wound therapy device having a conformable, reticulated manifold made of a porous and permeable material with a pattern of cuts configured to transform the manifold from a planar relaxed state to a pliable three-dimensional state when the manifold is extended along a lateral axis. The manifold further may have a perimeter border substantially free of the pattern of cuts. The manifold may also have at least one tab on at least one side of the lateral axis of the manifold. The tabs further may have an adhesive that adheres to the patient on one side of the device. The tabs may be made of a polymer or a plastic, including, but not limited to, an acrylic. In some embodiments, the manifold includes a reticulated polyurethane foam. In one embodiment, the polyurethane foam may have 40-50 pores per inch for optimal porosity and transfer of wound fluids while under reduced pressure.

In some embodiments, the manifold forms a geodesic dome when extended to the pliable three-dimensional state. The cuts in the manifold may appear in various geometries in both the planar relaxed state and the pliable three-dimensional state. In one embodiment, the cuts appear as a straight line when the manifold is in the planar relaxed state. In another embodiment, the cuts appear as substantially diamond-shaped when the manifold is extended along the lateral axis. In yet another embodiment, the cuts appear as substantially circular when the manifold is extended along the lateral axis. In some embodiments, the cuts substantially appear as one or more geometric shapes. The manifold may be extended along the lateral axis at a midpoint of the manifold.

The manifold of the present technology may be sized to fit a specific anatomy in the three-dimensional state. For example, some specific three-dimensional anatomies with asymmetric or non-planar shapes or sizes include, but are not limited to, a knee, an ankle, a shoulder, a breast, or an elbow.

In one embodiment, the manifold is elliptical in the planar relaxed state. In another embodiment, the manifold is circular in the planar relaxed state.

In an alternative embodiment, the manifold has a first layer with a pattern of cuts and a second layer with a pattern of cuts, where the patterns of cuts on the two layers do not align when both layers are in the pliable three-dimensional state. In another alternative embodiment, the device has an adhesive thermoformed outer polyurethane film that can be peeled away from a non-adhesive, disposable layer immediately prior to administration of the device, otherwise known as a "peel and place" device.

In accordance with another aspect of the present disclosure, a wound therapy kit is described. The kit may include: (i) a conformable, reticulated manifold made of a porous and permeable material, where the manifold has a pattern of cuts configured to transform the manifold from a planar relaxed state to a pliable three-dimensional state when the manifold is extended along a lateral axis, (ii) a wound interface layer, (iii) an adhesive, breathable drape; and (iv) a pneumatic connection to a negative pressure wound therapy device. In certain embodiments of the kit, the wound interface layer is made of a Milliken fabric. In yet another embodiment, the wound interface layer is made of a perforated silicone.

In accordance with yet another aspect of the present disclosure, a method for wound therapy is described. The method may include: (i) extending a conformable, reticulated manifold along a lateral axis of the manifold, wherein the manifold is made of a porous and permeable material and a pattern of cuts designed to transform the manifold from a planar relaxed state to a pliable three-dimensional state as the manifold is extended along the lateral axis; (ii) ceasing extension when the manifold bends to a desired pliable three-dimensional shape adaptable to a contoured wound site; (iii) placing the manifold in the desired pliable three-dimensional shape on the contoured wound site; (iv) placing an adhesive, breathable drape over the manifold on the contoured wound site; (v) attaching a pneumatic connection operatively coupled to a negative pressure wound therapy device to the adhesive, breathable drape; and (vi) activating the negative pressure wound therapy device to apply a negative pressure environment to the wound site.

In one embodiment of the wound therapy method, the pneumatic connection attaches to the adhesive, breathable drape via a T.R.A.C. Pad™. The manifold also may have a perimeter border substantially free of the pattern of cuts. The manifold may also have at least one plastic tab on at least one side of the lateral axis of the manifold. The plastic tabs further may indicate where a user should grip to extend the manifold. The cuts may each appear as a straight line when the manifold is in the planar relaxed state. The cuts also may each appear as substantially diamond-shaped when the manifold is extended along the lateral axis. The cuts also may appear as substantially circular when the manifold is extended along the lateral axis. In some embodiments, the cuts may substantially appear as one or more geometric shapes.

In one embodiment of the method, the manifold has a first layer with a pattern of cuts and a second layer with a pattern of cuts, wherein the pattern of cuts of the first layer do not align with the pattern of cuts of the second layer when both layers are extended to the desired three-dimensional state. The manifold also may be extended along the lateral axis at a midpoint of the manifold.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

The wound therapy device, kit, and method of the present invention provides simple dressing administration to three-dimensional anatomy, decreasing kinks and poor adhesion of the device when used in tandem with a negative pressure source. The device and kit are also easily shipped in planar form, alleviating bulk shipments and providing for more efficient transport and storage.

Device

Referring generally to the FIGURES, a wound therapy device, kit, and method and components thereof are shown, according to various exemplary embodiments.

Figure 1:
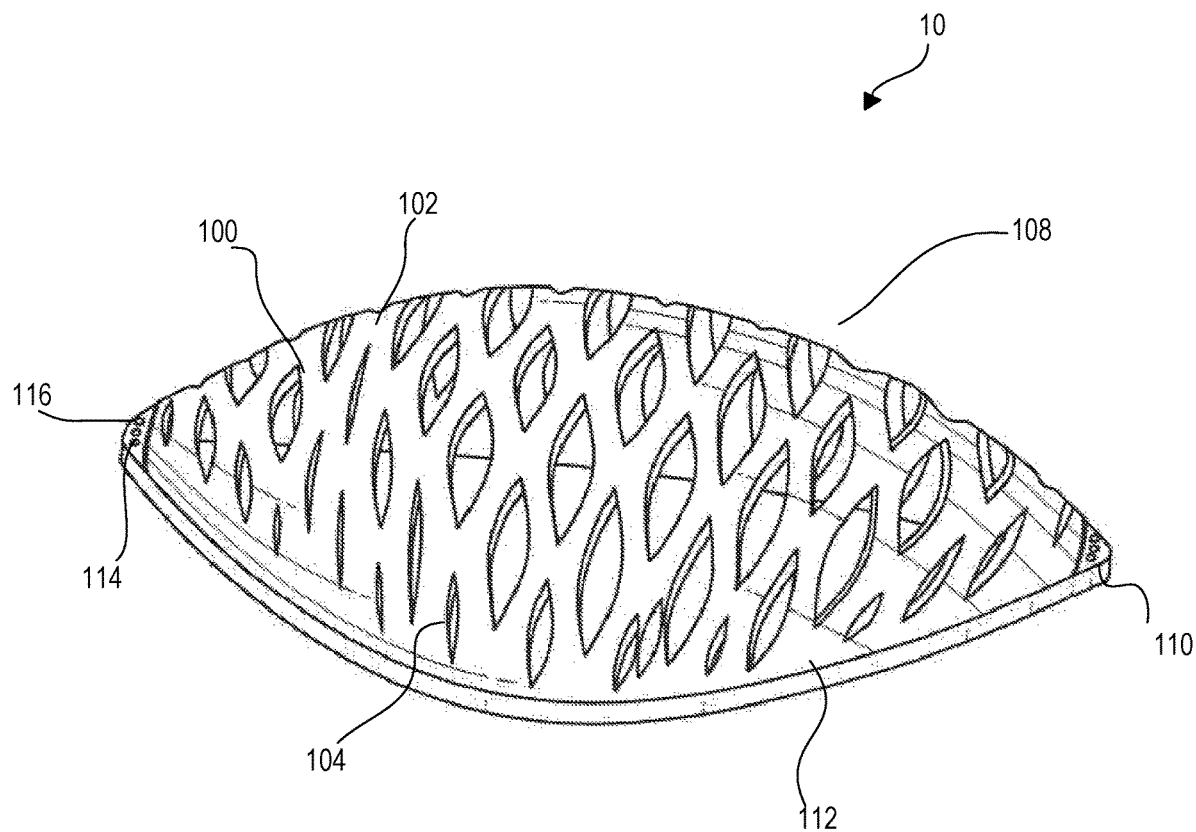
FIG. 1 is a front view of the wound therapy device according to exemplary embodiments.
Figure 1A:
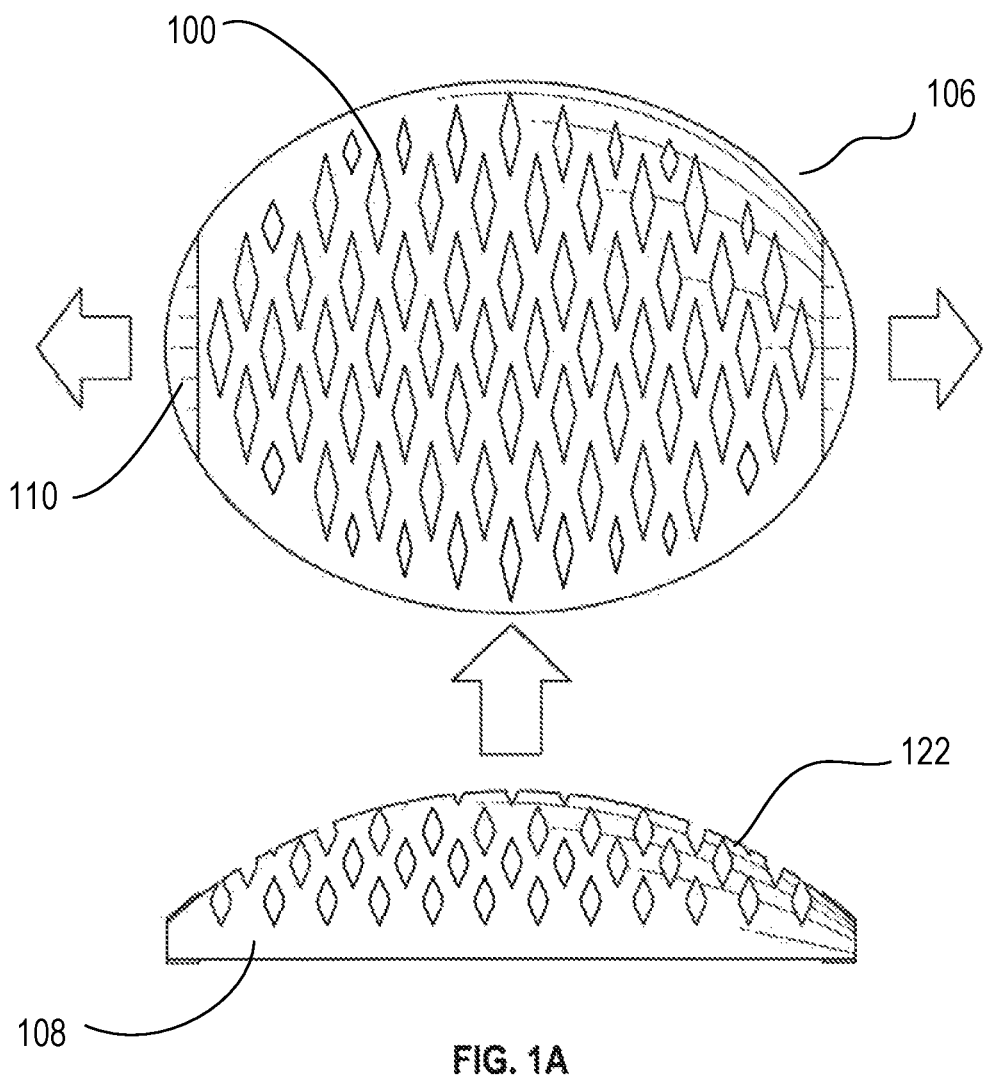
FIG. 1A is a top and side view, respectively, of the manifold extending from a planar relaxed state to a pliable three-dimensional geodesic dome when extended along a lateral axis.
Figure 1B:
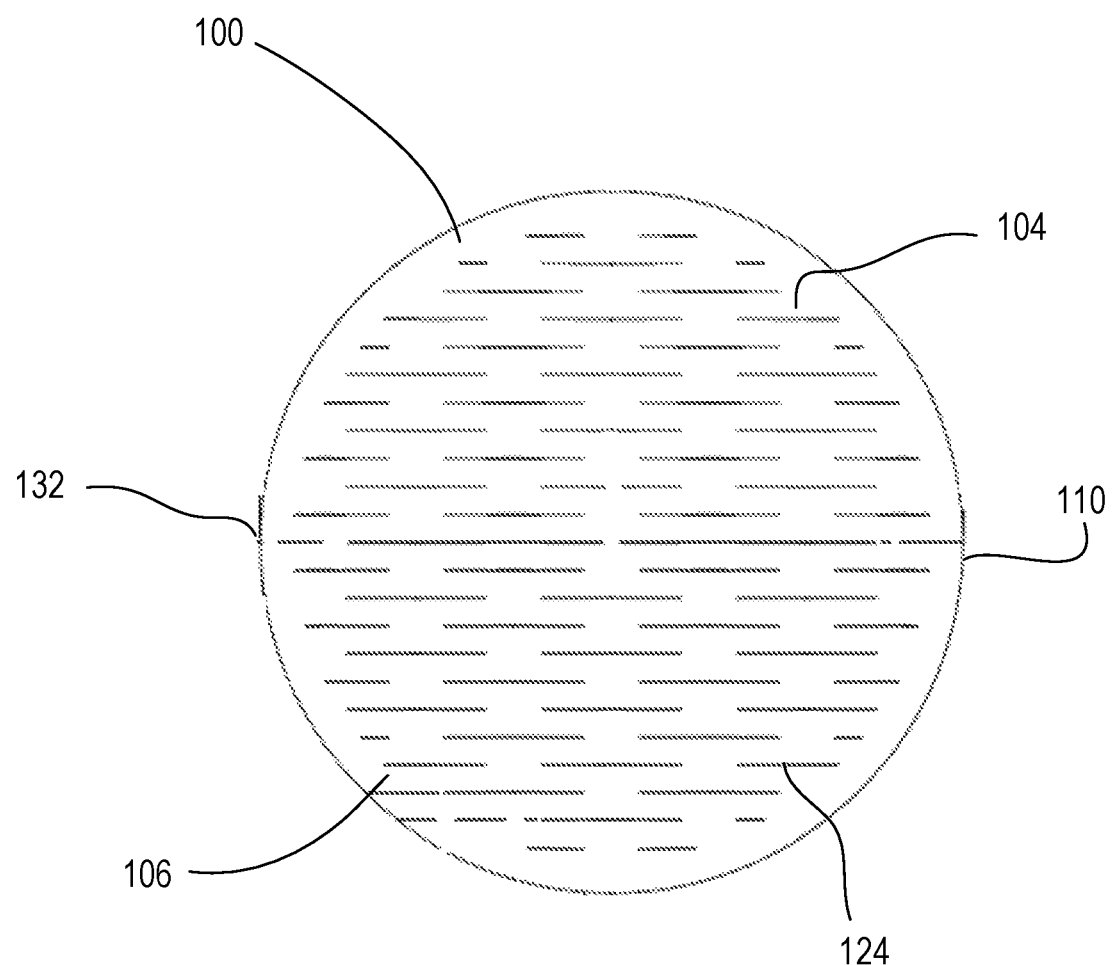
FIG. 1B is a top view of the manifold where the cuts each appear as a straight line when the manifold is in the planar relaxed state.
Figure 1C:
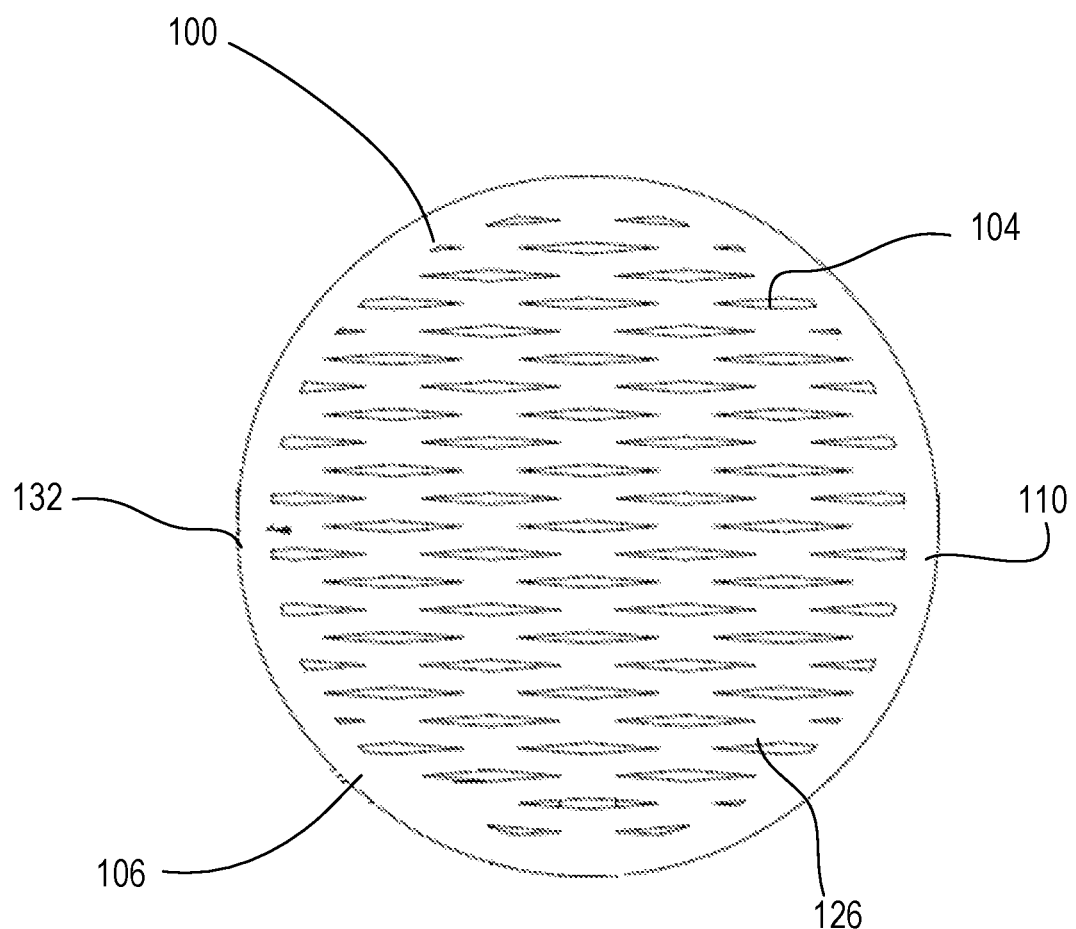
FIG. 1C is a top view of the device where the cuts each appear as substantially diamond-shaped when the manifold is extended along the lateral axis.
Figure 1D:
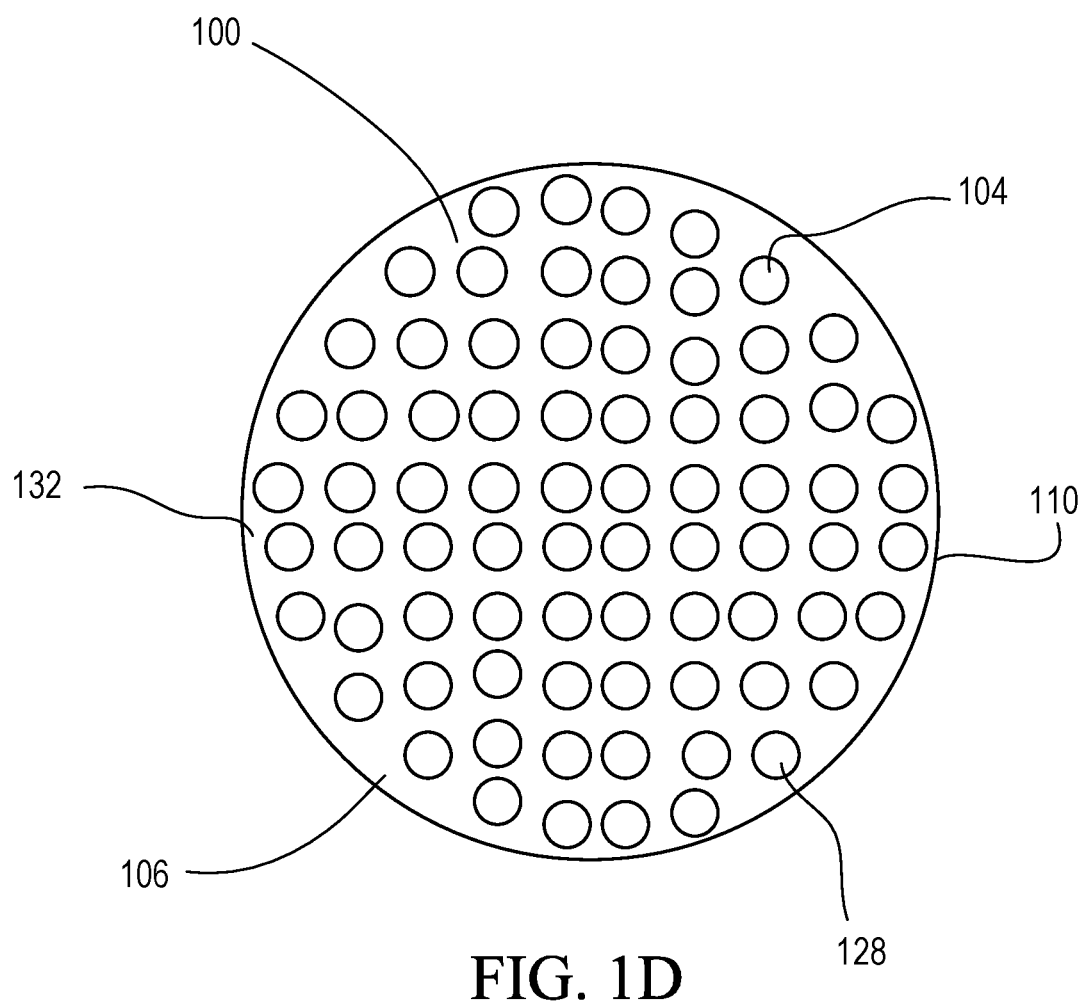
FIG. 1D is a top view of the device where the cuts each appear as substantially circular when the manifold is extended along the lateral axis.
Figure 1E:
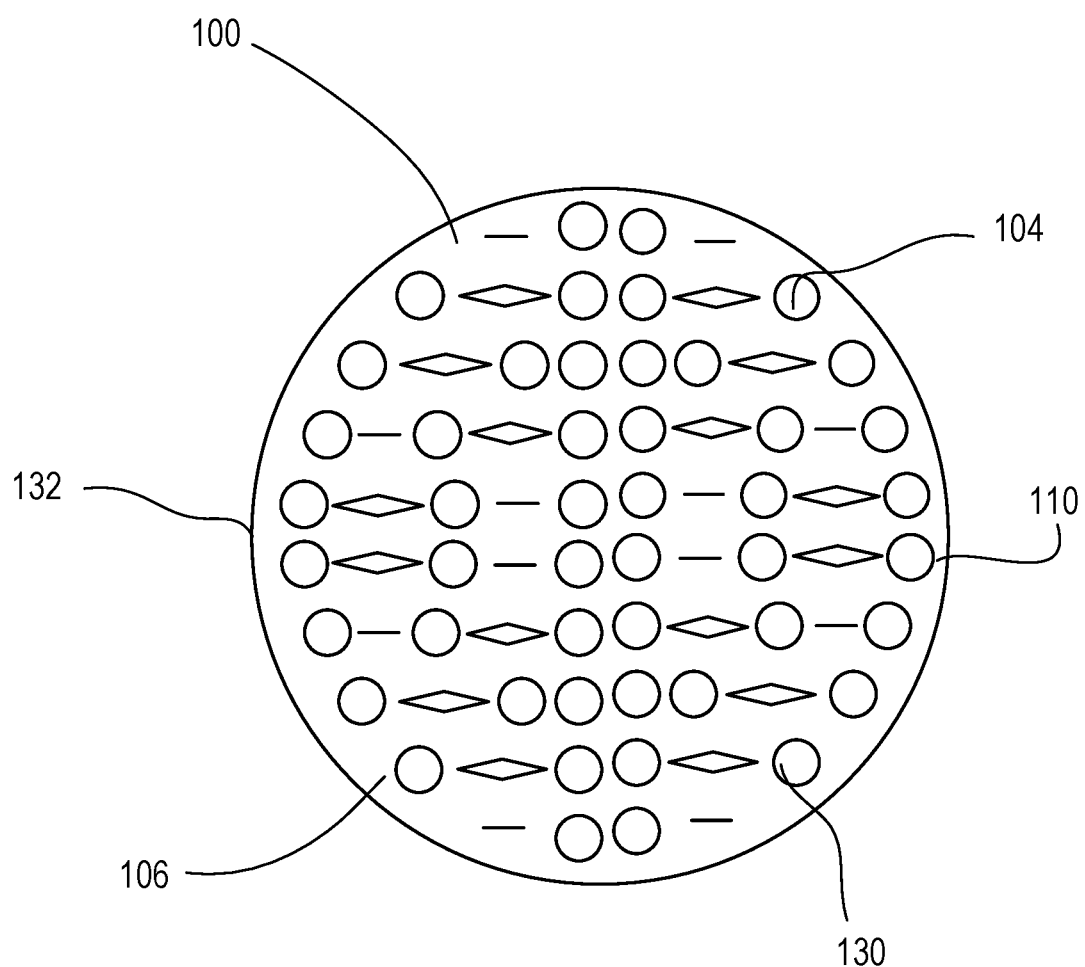
FIG. 1E is a top view of the device where the cuts each appear as one or more geometric shapes.

Referring to FIGS. 1-1E, an exemplary device used for wound therapy in accordance with the principles of the present disclosure is described. FIG. 1 is a front view of wound therapy device 10 according to two exemplary embodiments. Device 10 includes conformable, reticulated manifold 100 including porous and permeable material 102. Manifold 100 further includes pattern of cuts 104 designed to transform manifold 100 from planar relaxed state 106, shown in FIG. 7, to pliable three-dimensional state 108 when manifold 100 is extended along lateral axis 110.

FIG. 1 further illustrates that manifold 100 may include perimeter border 112 substantially free of the pattern of cuts. Device 10 further may include at least one plastic tab 114 on at least one side 116 of lateral axis 110 of manifold 100. One or more tabs 114 also may have an adhesive on a side of the device that adheres to a patient. One or more tabs 114 can also be made of an acrylic, or other exemplary materials used in wound therapy and dressings. In some embodiments, manifold 100 may be made of a reticulated polyurethane foam with specific porosities, e.g., illustratively 40-50 pores per inch. Porous and permeable material 102 may be any material that allows for good transfer of wound fluids while under reduced pressure.

FIG. 1A is a top and side view, respectively, of manifold 100 extending from planar relaxed state 106 to pliable three-dimensional state 108 when extended along lateral axis 110. FIG. 1A further illustrates manifold 100 forming geodesic dome 122 in pliable three-dimensional state 108. Geodesic dome 122 may be shaped to form-fit a variety of anatomies.

FIGS. 1B-1E illustrate various embodiments where pattern of cuts 104 on manifold 100 have different geometries to form different pliable three-dimensional states 108 when extended along lateral axis 110. The various patterns of cuts 104 create a multitude of arrays or shapes when extended into three dimensional state 108. FIG. 1B is a top view of device 10 where pattern of cuts 104 each appear as straight line 124 when manifold 100 is in planar relaxed state 106. FIG. 1C is a top view of device 10 where pattern of cuts 104 each appear as substantially diamond-shaped 126 when manifold 100 is extended along lateral axis 110. FIG. 1D is a top view of device 10 where pattern of cuts 104 each appear as substantially circular 128 when manifold 100 is extended along lateral axis 104. FIG. 1E is a top view of device 10 where pattern of cuts 104 each appear as one or more geometric shapes 130. Manifold 100 may be extended along lateral axis 110 at midpoint 132 of manifold 100.

Manifold 100 in pliable three-dimensional state 108 may be sized to fit a number of specific anatomies. For example, 10 device may fit a knee, an ankle, a shoulder, a breast, or an elbow when manifold 100 is extended in pliable three-dimensional state 108.

Figure 2:
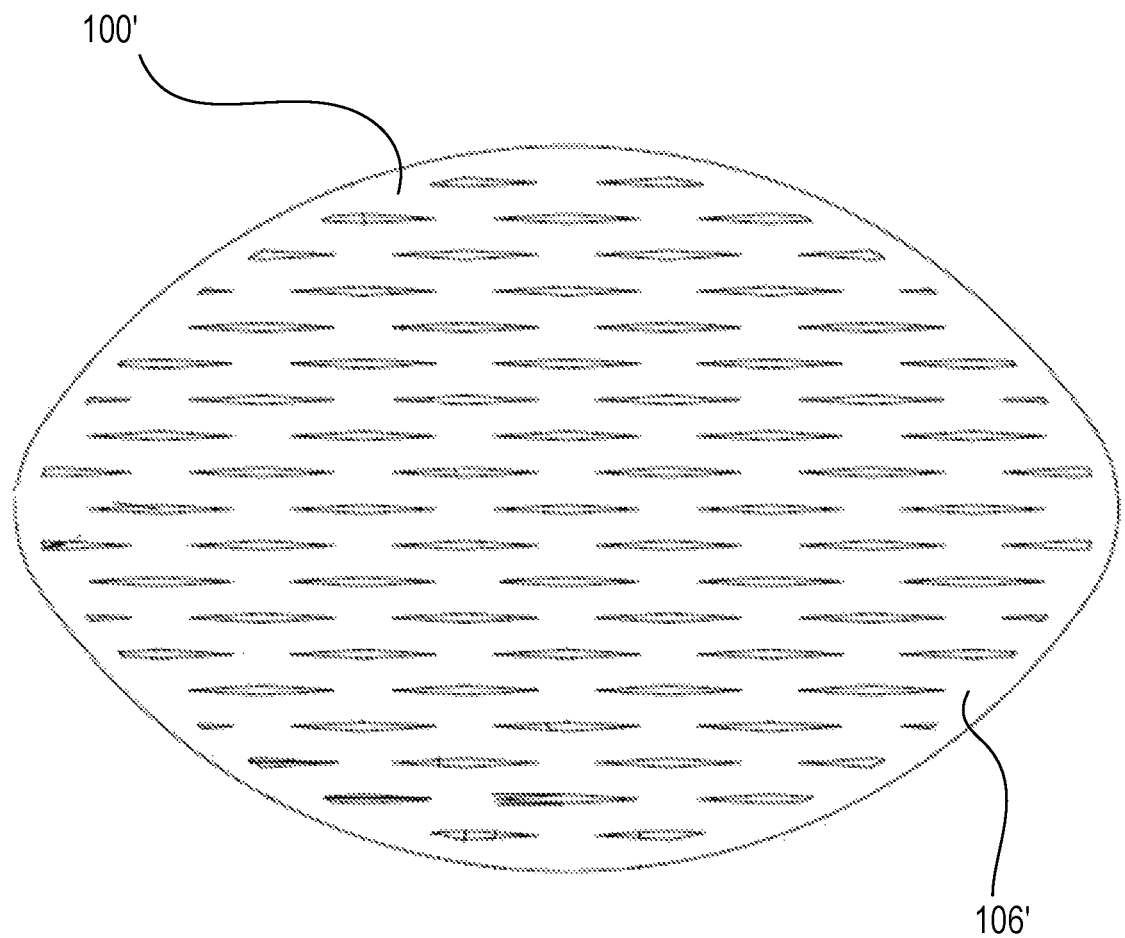
FIG. 2 is a top view of the device where the manifold is elliptical in the planar relaxed state.

FIG. 2 is a top view of device 10 where, in one embodiment, manifold 100' is elliptical in planar relaxed state 106'.

Figure 3:
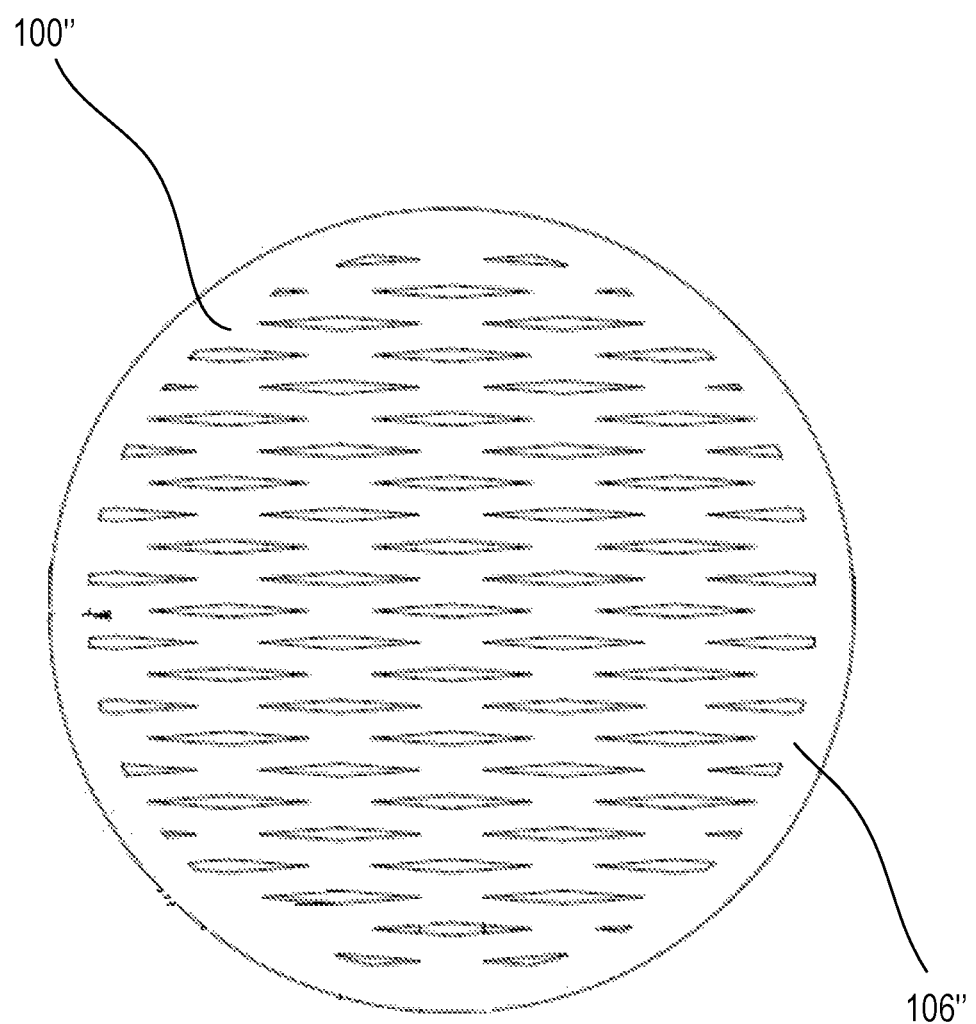
FIG. 3 is a top view of the device where the manifold is circular in the planar relaxed state.

FIG. 3 is a top view of device 10 where manifold 100" is circular in planar relaxed state 106".

Figure 4:
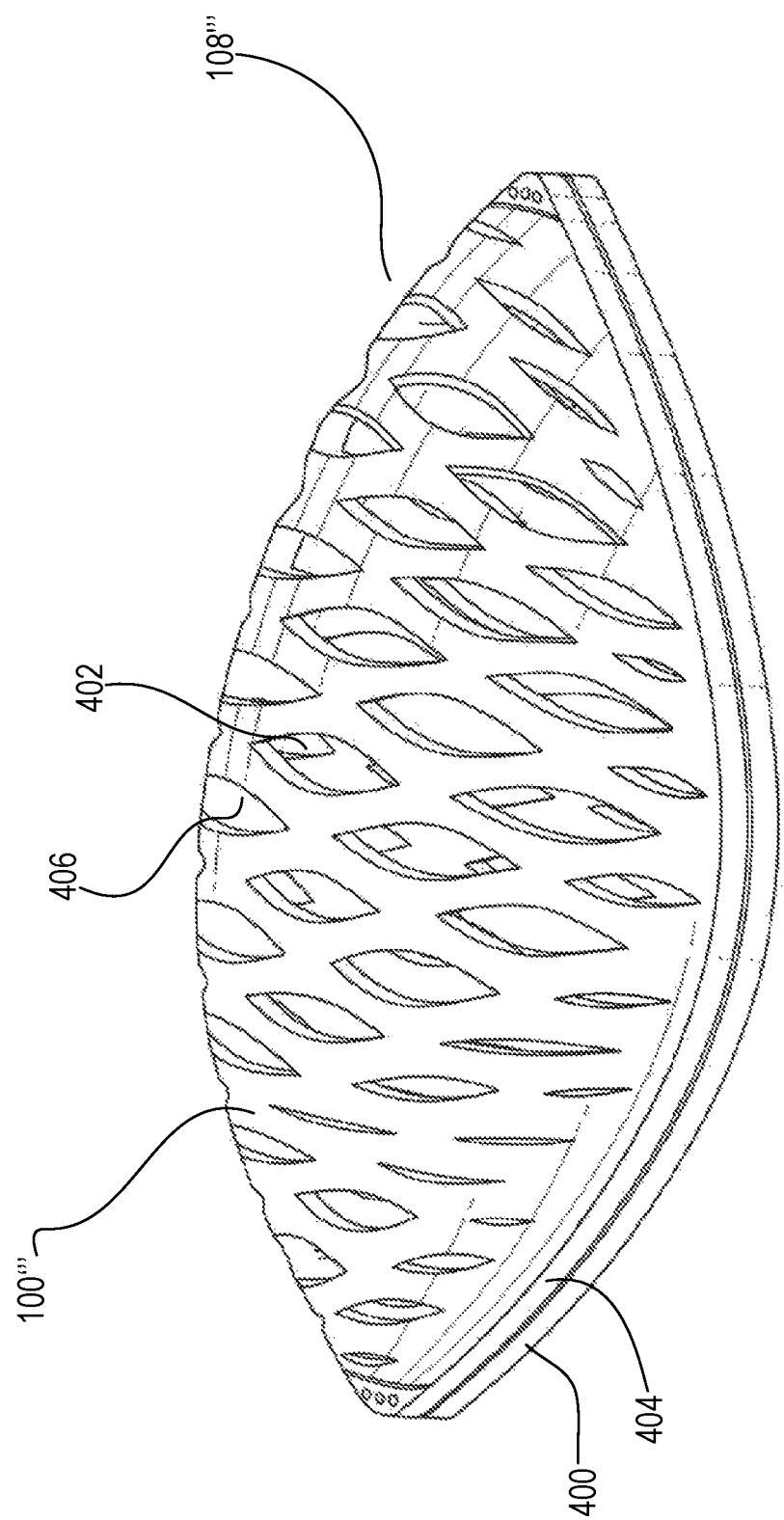
FIG. 4 is a front view of the device where the manifold has a first layer with a pattern of cuts and a second layer with a pattern of cuts, where the pattern of cuts of the first layer do not align with the pattern of cuts of the second layer when both layers are in the pliable three-dimensional state.

FIG. 4 depicts a front view of a multiple layer embodiment where manifold 100''' includes first layer 400 with pattern of cuts 402 and second layer 404 with pattern of cuts 406, where pattern of cuts 402 of first layer 400 does not align with pattern of cuts 406 of second layer 404 when both layers are in pliable three-dimensional state 108'''. The layers may be arranged such that as manifold 100''' forms a complex curve, the open areas in one layer line up with the closed areas in the second layer. This helps ensure no contact between polyurethane manifold 100''' and the wound bed.

Figure 5:
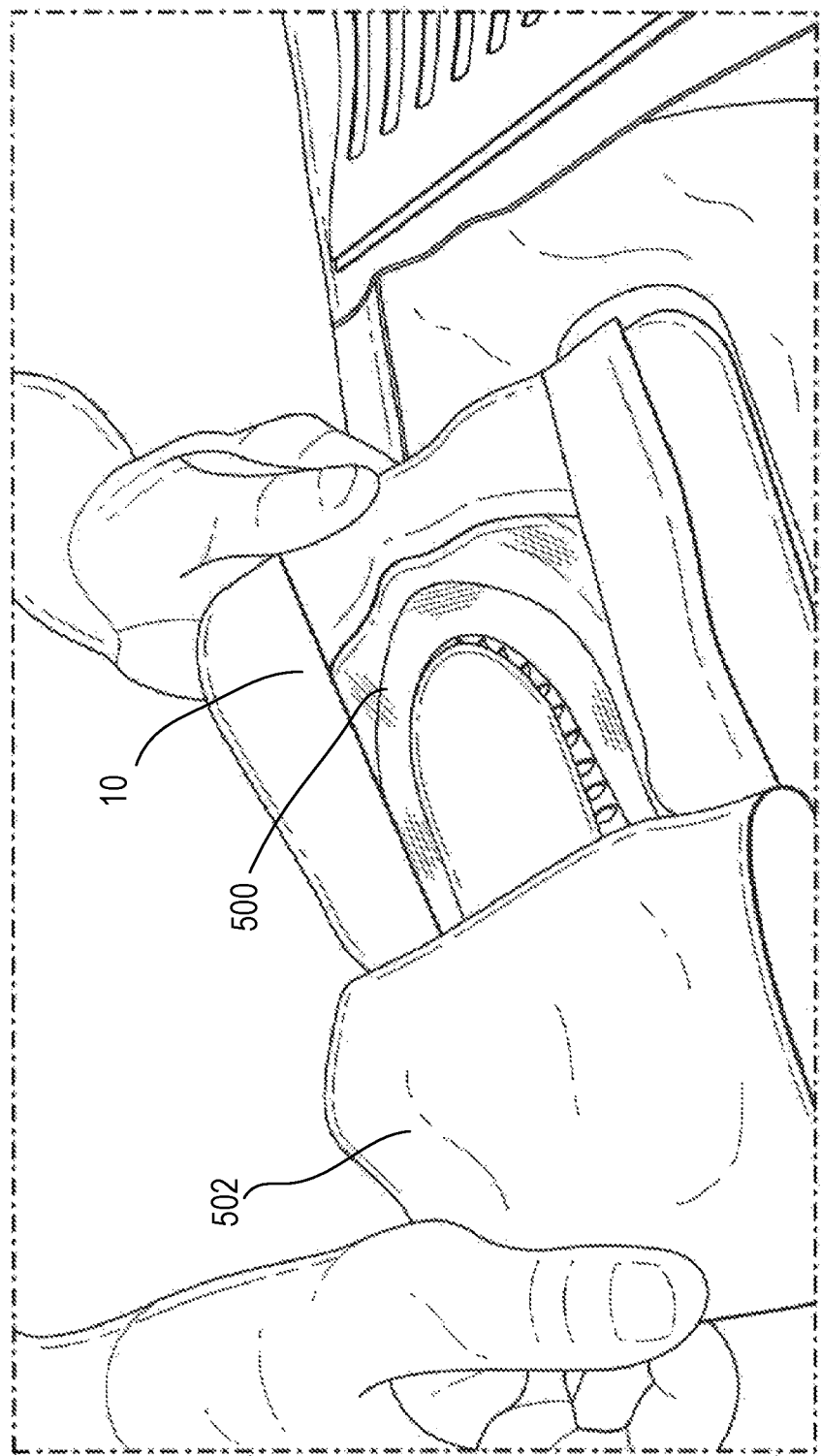
FIG. 5 is a perspective view of the device with an adhesive thermoformed outer polyurethane film configured to be peeled away from a non-adhesive, disposable layer immediately prior to administration of the device.

Referring now to FIG. 5, a "peel and place" embodiment of device 10 is depicted. Here, device 10 further may include adhesive, thermoformed outer polyurethane film 500 designed to be peeled away from non-adhesive, disposable layer 502 immediately prior to administration of device 10 on a wound bed. The "peel and place" embodiment allows for easy shipment of the device, increased sterility, and usage at any desired time by the patient or medical practitioner.

Kit

Figure 6:
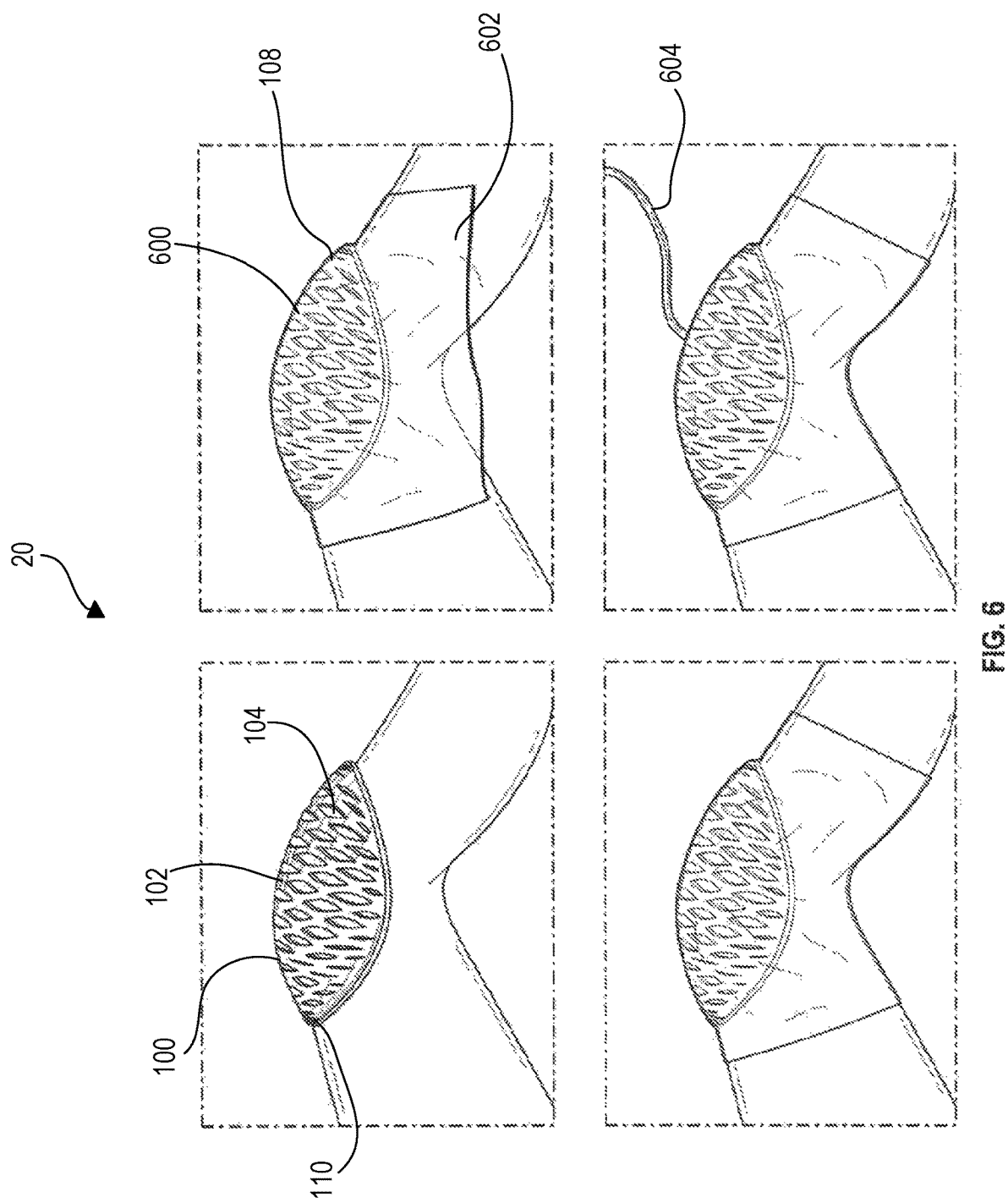
FIG. 6 illustrates an exemplary embodiment of the wound therapy kit, including: (i) the conformable, reticulated manifold; (ii) a wound interface layer; (iii) an adhesive, breathable drape; and (iv) a pneumatic connection to a negative pressure wound therapy device.

Referring now to FIG. 6, wound therapy kit 20 in accordance with the principles of the present disclosure is described. Wound therapy kit 20 includes: (i) conformable reticulated manifold 100 including porous, permeable material 102 where the manifold has pattern of cuts 104 designed to transform manifold 100 from planar relaxed state 106, shown in FIG. 7, to pliable three-dimensional state 108 when manifold 100 is extended along lateral axis 110; (ii) wound interface layer 600; (iii) adhesive, breathable drape 602; and (iv) pneumatic connection 604 to a negative pressure wound therapy device.

In certain embodiments, wound interface layer 600 may be made of a Milliken fabric. In other embodiments, wound interface layer may be made of a perforated silicone.

Method

Figure 7:
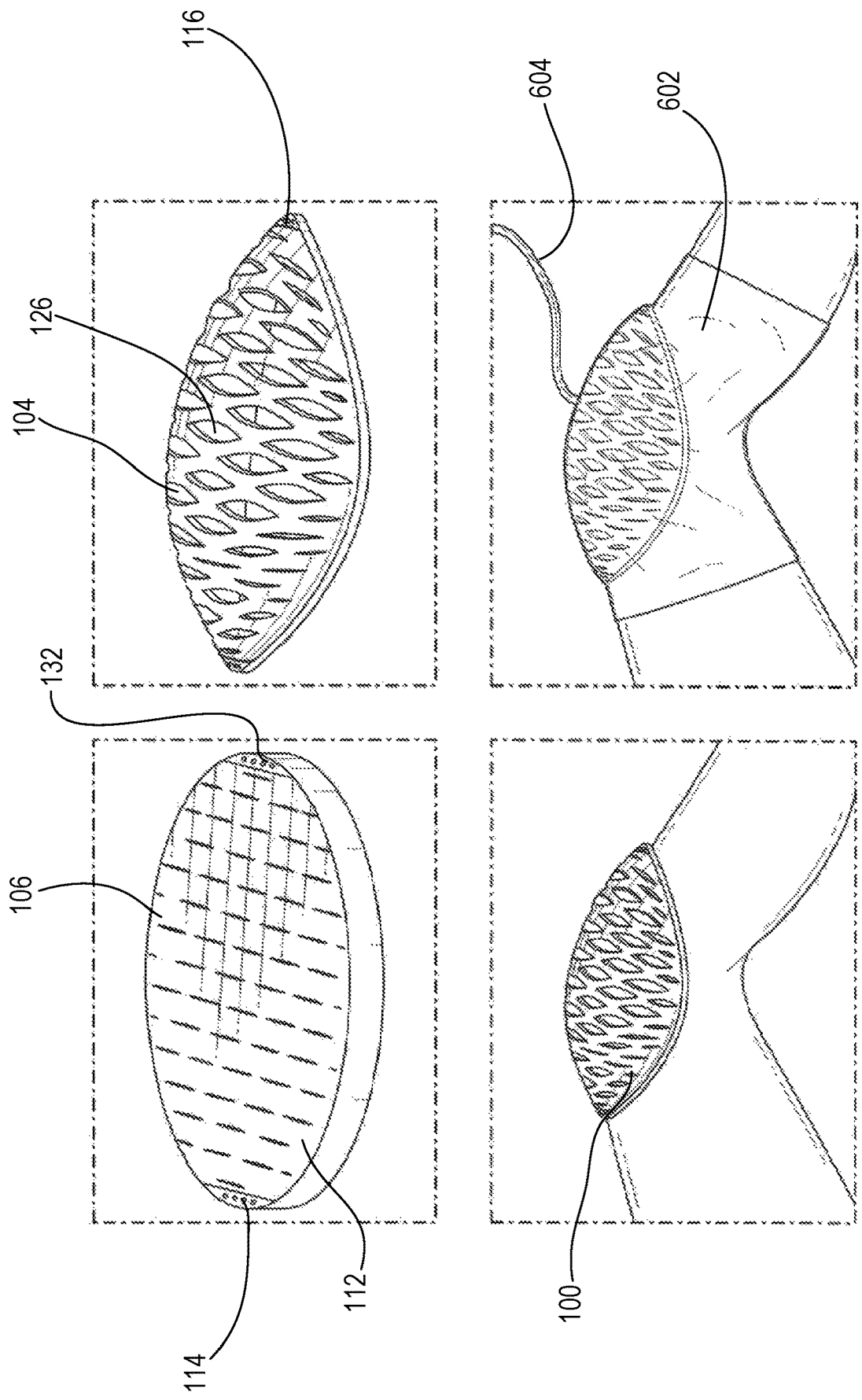
FIG. 7 illustrates an exemplary embodiment of the method for wound therapy.

Referring now to FIG. 7, a method for wound therapy in accordance with the principles of the present disclosure is described. This method provides for a more form-fitting and adaptable type of NPWT that can work with anatomies that previously adjusted poorly with NPWT. The method includes: (i) extending conformable, reticulated manifold 100 along lateral axis 110 of manifold 100, where manifold 100 may be made of porous and permeable material 102 and pattern of cuts 104 designed to transform manifold 100 from planar relaxed state 106 to pliable three-dimensional state 108 as manifold 100 is extended along lateral axis 110; (ii) ceasing extension when manifold 100 bends to desired pliable three-dimensional shape 108 adaptable to a contoured wound site; (iii) placing manifold 100 in desired pliable three-dimensional shape 108 on the contoured wound site; (iv) placing adhesive, breathable drape 602 over manifold 100 on the contoured wound site; (v) attaching pneumatic connection 604 operatively coupled to a negative pressure wound therapy device to adhesive, breathable drape 602; and (vi) activating a negative pressure wound therapy device to apply a negative pressure environment to the wound site.

In FIG. 7, pneumatic connection 604 may attach to adhesive breathable drape 602 via a T.R.A.C. Pad™. The method further may include perimeter border 112 substantially free of pattern of cuts 104. Manifold 100 further may have at least one plastic tab 114 on at least one side of lateral axis 116 of manifold 100. One or more plastic tab 114 also may indicate where a user grips to extend manifold 100.

Similar to embodiments for device 10, cuts 104 may appear as a straight line when manifold 100 is in planar relaxed state 106. Pattern of cuts 104 also may appear as substantially diamond-shaped 126 when manifold 100 is extended along lateral axis 110. Pattern of cuts 104 also may appear as substantially circular 128, as depicted in FIG. 1D, when manifold 100 is extended along lateral axis 110. Also, pattern of cuts 104 may be one or more geometric shapes 130, as depicted in FIG. 1E. Manifold 100 also may have a first layer 400 with pattern of cuts 402 and second layer 404 with pattern of cuts 406, where pattern of cuts 402 of first layer 400 do not align with pattern of cuts 406 of second layer 404 when both layers 400 and 404 are extended to desired pliable three-dimensional state 108, as depicted in FIG. 4. Manifold 100 may extend along lateral axis 110 at midpoint 132 of manifold 100 for improved extension of device 10.

Although the figures show a specific order of method steps, the order of the steps may differ from what is depicted. Also two or more steps can be performed concurrently or with partial concurrence. All such variations are within the scope of the disclosure.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

What is claimed is:

1. A wound therapy device comprising:
a conformable, reticulated manifold comprising a porous and permeable material, wherein the manifold further comprises a first layer with a pattern of cuts and a second layer with a pattern of cuts configured to transform the manifold from a planar relaxed state to a pliable three-dimensional state when the manifold is extended along a lateral axis, the pattern of cuts of the first layer being misaligned with the pattern of cuts of the second layer when the manifold is in the pliable three-dimensional state.

2. The device of claim 1, wherein the manifold further comprises a perimeter border substantially free of the pattern of cuts.

3. The device of claim 1, wherein the manifold comprises a reticulated polyurethane foam with 40-50 pores per inch.

4. The device of claim 1, wherein the manifold forms a geodesic dome in the pliable three-dimensional state.

5. The device of claim 1, wherein the cuts each appear as a straight line when the manifold is in the planar relaxed state.

6. The device of claim 1, wherein the cuts appear as substantially diamond-shaped when the manifold is extended along the lateral axis.

7. The device of claim 1, wherein the cuts appear as substantially circular when the manifold is extended along the lateral axis.

8. The device of claim 1, wherein the cuts comprise one or more geometric shapes.

9. The device of claim 1, wherein the manifold is extended along the lateral axis at a midpoint of the manifold.

10. The device of claim 1, wherein the manifold in the pliable three-dimensional state is sized to fit a knee, an ankle, a shoulder, a breast, or an elbow.

11. The device of claim 1, wherein the manifold is elliptical in the planar relaxed state.

12. The device of claim 1, wherein the manifold is circular in the two dimensional, planar relaxed state.

13. The device of claim 1, wherein the device further comprises an adhesive thermoformed outer polyurethane film configured to be peeled away from a non-adhesive, disposable layer immediately prior to administration of the device.

14. A wound therapy kit comprising:
a conformable, reticulated manifold comprising a porous and permeable material, wherein the manifold further comprises a first layer with a pattern of cuts and a second layer with a pattern of cuts configured to transform the manifold from a planar relaxed state to a pliable three-dimensional state when the manifold is extended along a lateral axis, the pattern of cuts of the first layer being misaligned with the pattern of cuts of the second layer when the manifold is in the pliable three-dimensional state;
a wound interface layer;
an adhesive, breathable drape; and
a pneumatic connection to a negative pressure wound therapy device.

15. The kit of claim 14, wherein the wound interface layer comprises Milliken fabric.

16. The kit of claim 14, wherein the wound interface layer comprises perforated silicone.

17. A method for wound therapy comprising:
extending a conformable, reticulated manifold along a lateral axis of the manifold, wherein the manifold comprises a porous and permeable material and a first layer with a pattern of cuts and a second layer with a pattern of cuts configured to transform the manifold from a planar relaxed state to a pliable three-dimensional state when the manifold is extended along a lateral axis, wherein the pattern of cuts of the first layer are not aligned with the pattern of cuts of the second layer when the manifold is in the pliable three-dimensional state;
ceasing extension when the manifold bends to a desired pliable three-dimensional shape adaptable to a contoured wound site;
placing the manifold in the desired pliable three-dimensional shape on the contoured wound site;
placing an adhesive, breathable drape over the manifold on the contoured wound site;
attaching a pneumatic connection operatively coupled to a negative pressure wound therapy device to the adhesive, breathable drape; and
activating the negative pressure wound therapy device to apply a negative pressure environment to the wound site.

18. The method of claim 17, wherein the manifold further comprises at least one plastic tab on at least one side of the lateral axis of the manifold and the plastic tabs indicate where a user grips to extend the manifold.

19. The method of claim 17, wherein the cuts each appear as a straight line when the manifold is in the planar relaxed state and appear as substantially diamond-shaped when the manifold is extended along the lateral axis.

20. The method of claim 17, wherein the cuts appear as substantially circular when the manifold is extended along the lateral axis.

21. The method of claim 17, wherein the cuts comprise one or more geometric shapes.

* * * * *